(12) United States Patent
Schmied et al.

(10) Patent No.: US 10,433,816 B2
(45) Date of Patent: Oct. 8, 2019

(54) METHOD AND SYSTEM FOR MANIPULATING MEDICAL DEVICE OPERATING PARAMETERS ON DIFFERENT LEVELS OF GRANULARITY

(71) Applicant: General Electric Company, Schenectady, NY (US)

(72) Inventors: Heinz Schmied, Zipf (AT); Franz Mair, Zipf (AT); Mario Mlinaric, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 834 days.

(21) Appl. No.: 14/548,978

(22) Filed: Nov. 20, 2014

(65) Prior Publication Data

US 2016/0143608 A1 May 26, 2016

(51) Int. Cl.
*A61B 6/00* (2006.01)
*A61B 8/00* (2006.01)
*A61B 8/13* (2006.01)
*A61B 5/055* (2006.01)
*A61B 6/03* (2006.01)
*G16H 40/63* (2018.01)
*A61B 5/00* (2006.01)
*G06F 19/00* (2018.01)

(52) U.S. Cl.
CPC .............. *A61B 8/465* (2013.01); *A61B 6/465* (2013.01); *G16H 40/63* (2018.01); *A61B 5/055* (2013.01); *A61B 5/7475* (2013.01); *G06F 19/321* (2013.01)

(58) Field of Classification Search
CPC ....... A61B 8/465; A61B 6/465; A61B 5/7475; G06F 19/3406; G06F 19/321
See application file for complete search history.

(56) References Cited

U.S. PATENT DOCUMENTS

| | | | |
|---|---|---|---|
| 5,315,999 A | 5/1994 | Kinicki et al. | |
| 6,599,244 B1 | 7/2003 | Epps et al. | |
| 2002/0173721 A1* | 11/2002 | Grunwald | A61B 8/00 600/437 |
| 2007/0046649 A1* | 3/2007 | Reiner | G06F 3/03545 345/173 |
| 2008/0312953 A1* | 12/2008 | Claus | G06F 19/3406 705/2 |
| 2011/0078201 A1 | 3/2011 | Ryan et al. | |
| 2014/0088428 A1* | 3/2014 | Yang | A61B 8/4444 600/443 |

* cited by examiner

*Primary Examiner* — Katherine L Fernandez
(74) *Attorney, Agent, or Firm* — McAndrews, Held & Malloy, Ltd.; Jacob Groethe; David Bates (57) ABSTRACT

Various embodiments include a system and method for manipulating medical device operating parameters, stored in a hierarchical organization, at different levels of granularity. The method can include receiving, at a processor, first user input selecting an operating parameter of a medical device from a medical device user interface displayed at a display system. The method may include presenting, at the display system, a parameter presentation prompted by the operating parameter selection. In various embodiments, a plurality of setting values each corresponding to a different hierarchical level of the operating parameter is presented in the parameter presentation. The method may include receiving, at the processor, second user input manipulating a value of one of the setting values presented in the parameter presentation. The method can also include storing, at storage, the value of the manipulated setting value.

20 Claims, 9 Drawing Sheets

METHOD AND SYSTEM FOR MANIPULATING MEDICAL DEVICE OPERATING PARAMETERS ON DIFFERENT LEVELS OF GRANULARITY

CROSS-REFERENCE TO RELATED APPLICATIONS/INCORPORATION BY REFERENCE

[Not Applicable]

FIELD OF THE INVENTION

Certain embodiments of the invention relate to medical device operating parameters. More specifically, certain embodiments of the invention relate to a method and system for manipulating medical device operating parameters, stored in a hierarchical organization, at different levels of granularity.

BACKGROUND OF THE INVENTION

Medical devices, such as ultrasound, magnetic resonance imaging (MRI), computed tomography (CT), digital radiography, and/or X-ray imaging modalities, operate according to various parameters, many of which are user-definable. The operating parameters may be applicable to one or more systems, users, system component types, system sub-component types, application types, examination types, and the like. The settings corresponding to the operating parameters may, therefore, be stored in hierarchical levels. For example, image brightness may be an operating parameter applicable to different imaging systems, users of the imaging systems, applications, rendering usages, and rendering types, among other things. It may not be clear to a user adjusting the image brightness, however, whether the adjustment will be a global change for the system, specific to the user, specific to the application, specific to the rendering usage, or specific to the rendering type. A user desiring to make widespread operating parameter changes may suffer from frustration and decreased efficiency when the user discovers that the change was made for a limited application and the changes may need to be repeated. Similarly, a user attempting to achieve a limited operating parameter change may cause confusion and/or inefficiencies when the user or other users discover that unintended global changes were made.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for manipulating medical device operating parameters, stored in a hierarchical organization, at different levels of granularity, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a method and system for manipulating medical device operating parameters, stored in a hierarchical organization, at different levels of granularity. More specifically, aspects of the present invention have the technical effect of improving the configurability of a medical device by streamlining the process for setting operating parameters for different medical device operating situations.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

Figure 1:
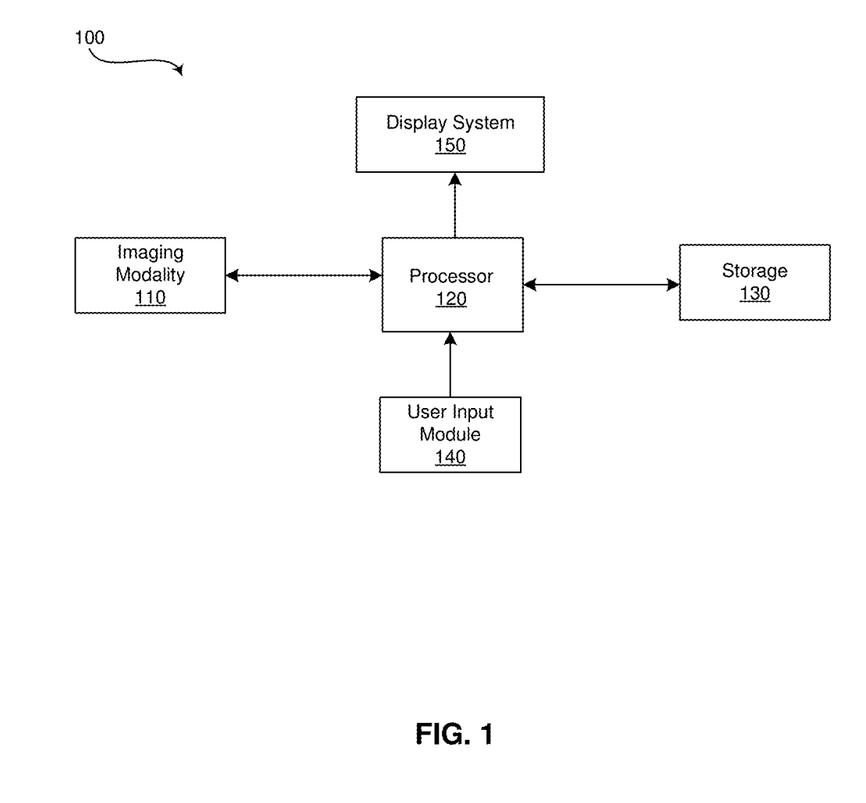
FIG. 1 is a block diagram of an exemplary medical imaging system having operating parameters stored in a hierarchical organization that may be manipulated at different levels of granularity, in accordance with an embodiment of the invention.

It should be noted that various embodiments are described herein with reference to operating parameters of imaging modalities. For example, FIG. 1 illustrates an exemplary medical imaging system and FIGS. 2-8 illustrate screenshots from a standard touch screen layout for a user interface of an ultrasound system. However, aspects of the present invention are not limited to imaging modalities, let alone ultrasound systems. Instead, any medical device having configurable operating parameters is contemplated. Moreover, in imaging modality embodiments, the imaging modality may be any suitable imaging modality, such as ultrasound, magnetic resonance imaging (MRI), computed tomography (CT), digital radiography, X-ray, and the like.

FIG. 1 is a block diagram of an exemplary medical imaging system 100 having operating parameters stored in a hierarchical organization that may be manipulated at different levels of granularity, in accordance with an embodiment of the invention. The system 100 includes an imaging modality 110, a processor 120, storage 130, a user input module 140, and a display system 150. The system 100 may include any number of imaging modalities 110, processors 120, storage components 130, user input modules 140, and display systems 150 and is not in any way limited to the embodiment of system 100 illustrated in FIG. 1. The components of the system 100 may communicate via wired and/or wireless communication, for example, and may be separate systems and/or integrated to varying degrees, for example.

The imaging modality 110 comprises suitable logic, circuitry, interfaces and/or code that may be operable to capture an image of a patient anatomy. For example, the imaging modality 110 may include an ultrasound scanner, magnetic resonance imager, X-ray imager, or the like. The imaging modality 110 acquires image data in response to operating parameters and instructions communicated by processor 120 to the imaging modality 110. The image data representative of acquired image(s) is communicated from the imaging modality 110 to the processor 120. The operating parameters, instructions, and image data may be communicated electronically over a wired or wireless connection, for example.

The storage 130 comprises suitable logic, circuitry, interfaces and/or code that may be operable to store medical device operating parameters, image data, and any other suitable information. The storage 130 may be one or more computer-readable memories, for example, such as a hard disk, floppy disk, CD, CD-ROM, DVD, compact storage, flash memory, random access memory, read-only memory, electrically erasable and programmable read-only memory and/or any suitable memory. The storage 130 may include databases, libraries, sets of information, or other storage accessed by and/or incorporated with the processor 120, for example. The storage 130 may be able to store data temporarily or permanently, for example. In various embodiments, the storage 130 stores one or more software applications.

The user input module 140 comprises suitable logic, circuitry, interfaces and/or code that may be operable to communicate information from a user and/or at the direction of the user to the processor 120 of the system 100, for example. The user input module 140 may include button(s), a touchscreen, motion tracking, voice recognition, a mousing device, keyboard, camera and/or any other device capable of receiving a user directive. In certain embodiments, one or more of the user input modules 140 may be integrated into other components, such as the display system 150, for example. As an example, user input module 140 may include a touchscreen display. In various embodiments, the user input module 140 may provide operating parameter setting values for an imaging modality 110 or other medical device to processor 120. The operating parameters may be used to operate the imaging modality 110 to acquire image data, for example.

The display system 150 comprises suitable logic, circuitry, interfaces and/or code that may be operable to communicate visual information to a user. For example, a display system 150 may include one or more monitors comprising a liquid crystal display, a light emitting diode display, and/or any suitable display. The display system 150 can be operable to display a medical device user interface 200 for selecting an examination type 210 and setting operating parameter 220 setting values 236, 237, 238 as discussed below with reference to FIGS. 2-8, or any suitable information. The display system 150 may be operable to display image data acquired by imaging modality 110 and processed by processor 120, for example.

The processor 120 comprises suitable logic, circuitry, interfaces and/or code that may be operable to control the imaging modality 110 based at least in part on operating parameters and process image data acquired by imaging modality 110 for generating an image for presentation on a display system 150. The processor 120 may be one or more central processing units, microprocessors, microcontrollers, and/or the like. The processor 120 may be an integrated component, or may be distributed across various locations, for example. The processor 120 may be capable of executing any of the method(s) 300 and/or set(s) of instructions discussed below in accordance with the present invention, for example.

In operation, a user may navigate medical device user interface menus displayed at display system 150 using a user input module 140 to select, set, or otherwise manipulate operating parameters of the medical device 110 that are stored in a hierarchical organization at storage 130. For example, each operating parameter may be organized in a hierarchy. An operating parameter can have setting values at one or more levels in the hierarchy. As an example, a highest level of the hierarchy may be a system level, such as a particular medical device. Another level of the hierarchy can be a user level, such as a particular user of the medical device. Other levels may include levels associated with various optional or interchangeable components and subcomponents of the medical device, such as a type of transducer and/or a type of probe used in an ultrasound system, for example. Additional levels may relate to various application or examination types, such as an obstetric ultrasound application performed at a first trimester. In various embodiments, different operating parameters may have a different number of parameter levels. For example, some operating parameters may be system level parameters having one level, whereas other operating parameters can have multiple levels, such as two, six, ten, or any suitable number of levels. As described in detail below with regard to FIGS. 2-8, the setting values associated with each level are consistent with and/or fit within the setting values of the next level above, except for the highest system level, which may be constrained by the maximum and minimum values of the imaging modality 110 or other medical device.

Still referring to FIG. 1, the processor 120 may receive a selection of a setting value of an operating parameter at a particular parameter level. For example, button depressions, touchscreen selections, mousing inputs, keyboard inputs, and/or voice commands, among other things, may be received from the user input module 140 and processed by the processor 120 to select or modify a setting value of an operating parameter at a particular level. In response to the selection, the processor updates the setting value of the parameter at the particular level and if necessary, updates setting values of levels above and/or below the particular level to maintain consistency within the hierarchical organization. The updated setting value at the particular level and any other levels are stored in storage 130. The processor 120 retrieves and applies the appropriate operating parameters when executing an examination with the imaging modality 110 or other medical device.

Figure 2:
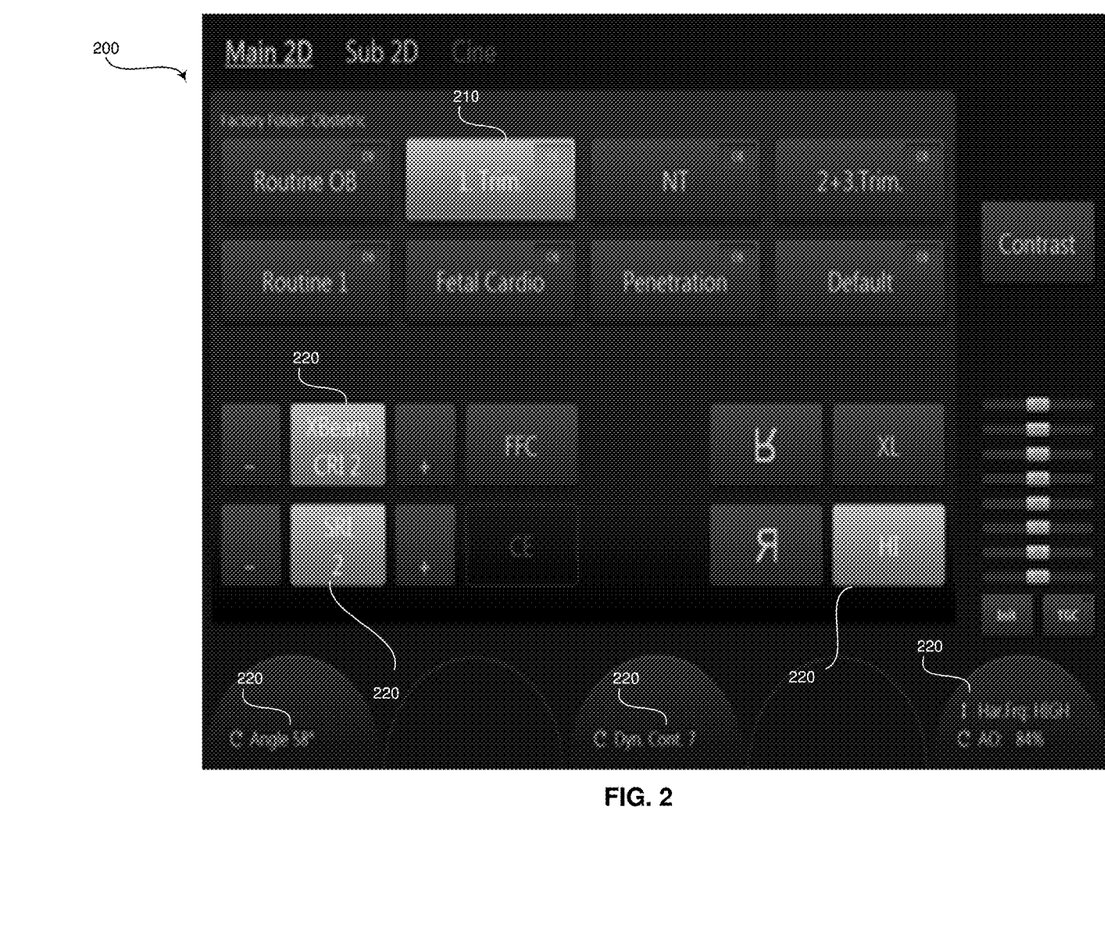
FIG. 2 illustrates an exemplary medical device user interface, in accordance with an embodiment of the invention.
Figure 3:
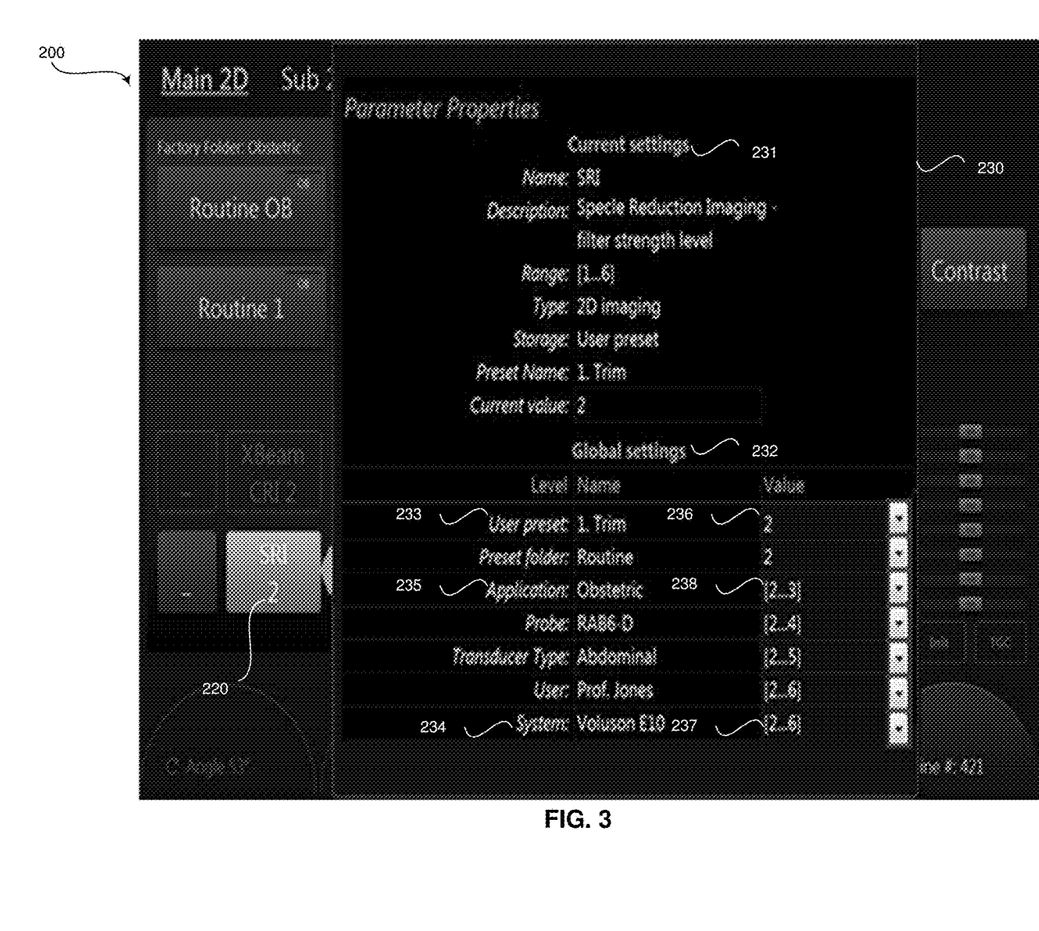
FIG. 3 illustrates an exemplary parameter presentation corresponding with a speckle reduction imaging filter strength level operating parameter selected from the medical device user interface of FIG. 2, in accordance with an embodiment of the invention.
Figure 4:
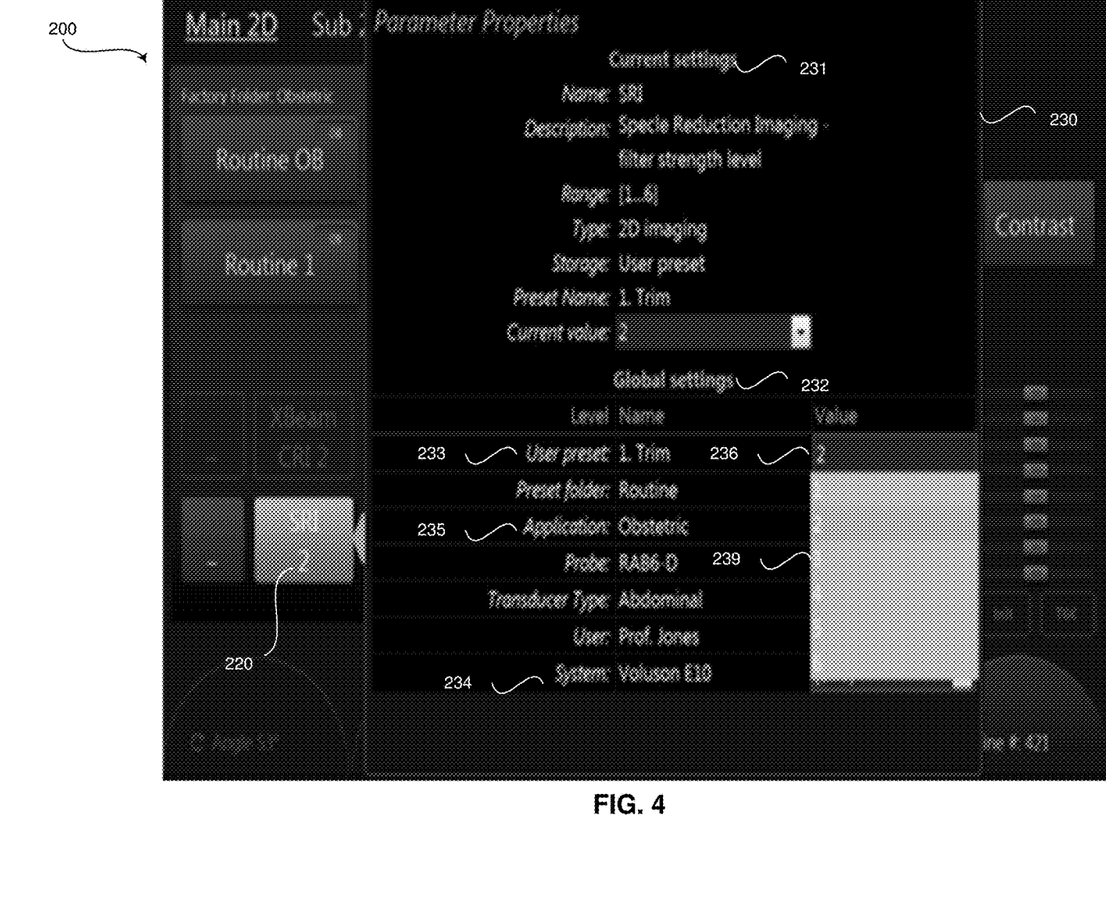
FIG. 4 illustrates an exemplary drop-down selection menu operable to select a setting value in an exemplary parameter presentation corresponding with a speckle reduction imaging filter strength level operating parameter selected from a medical device user interface of FIG. 2, in accordance with an embodiment of the invention.

FIG. 2 illustrates an exemplary medical device user interface 200, in accordance with an embodiment of the invention. FIG. 3 illustrates an exemplary parameter presentation 230 corresponding with a speckle reduction imaging filter strength level operating parameter 220 selected from the medical device user interface 200 of FIG. 2. FIG. 4 illustrates an exemplary drop-down selection menu 239 operable to select a setting value 236 in an exemplary parameter presentation 230 corresponding with a speckle reduction imaging filter strength level operating parameter 220 selected from a medical device user interface 200 of FIG. 2.

Referring to FIGS. 2-4, a medical device user interface 200 comprises selectable examination types 210 and operating parameters 220 corresponding with the selected examination type 210. For example, a user of imaging modality 110 or any suitable medical device may navigate through a medical device user interface 200 to select an examination type 210 and manipulate associated operating parameters 220. With reference to FIG. 2, a user of an ultrasound imaging modality 110 having an abdominal transducer type configured for an obstetric application may select various examinations 210 such as a first trimester examination, a nuchal translucency (NT) examination, a fetal cardiac imaging examination, a second and third trimester examination, a penetration examination, a routine examination, or a default examination, among other things. Each of the examination types 210 may have corresponding operating parameters 220, such as cross beam compound resolution imaging parameters (XBeam CRI) 220, speckle reduction imaging parameters (SRI) 220, and the like.

As illustrated in FIG. 3, selection of an operating parameter 220 prompts a parameter presentation 230 to be presented. The parameter presentation 230 may be, for example, a window, such as a pop-up window or any suitable visualization object. The parameter presentation 230 may include information regarding the current settings 231 of the selected operating parameter 220 and the global settings 232 presenting the hierarchical organization of the operating parameter 220. The global settings 232 may include one or more levels 233, 234, 235, each having associated setting values 236, 237, 238. For example, the levels may include a current level 233, a highest level 234, and one or more intermediary levels 235, although more or less levels are also contemplated. In various embodiments, the setting values 236, 237, 238 of the levels 233, 234, 235 are consistent such that setting values of lower levels are equal to or within the setting values of the higher levels. For example, the setting value 236 of 2 corresponding with the user preset level 233 is within the 2 . . . 3 range provided as the setting value 238 corresponding with the higher application level 235, which is within the 2 . . . 6 range provided as the setting value 237 corresponding with the highest system level 234. If a user desires to change the setting value 236 of the user preset level 233 to a value outside of the range of one or more higher levels, the setting values of the higher levels are changed to provide consistency. The changes to the higher levels may be automatic or a user may need to manually change the higher levels prior to being able to adjust the lower level setting value, for example. Similarly, changes to settings values 237, 238 associated with higher levels 234, 235 may initiate changes to setting values 236 of lower levels 233 to maintain consistency within the hierarchical organization of the operating parameter 220.

Referring to FIG. 4, a drop-down selection menu 239 is shown for selecting a setting value 236 associated with the user preset level 233. Although a drop-down selection menu 239 is shown, any suitable selection mechanism may be implemented, such as a text box, check boxes, radio buttons, and the like. The current value of 2 may be changed to a value in the range of 1 . . . 6. If a value is chosen outside of setting values or ranges associated with higher levels 234, 235, the setting values 237, 238 of the higher levels 234, 235 may be automatically updated to provide consistency between the setting values 233, 234, 235. For example, referring to FIG. 3, if the setting value 236 corresponding to the user preset level 233 is changed to 1, the levels above the user preset level 233 are modified to provide consistency within the operating parameter hierarchical organization. Specifically, the preset folder level would change to a 1 setting value, the application level 235 would change to a 1 . . . 3 setting value 238, the probe level would change to a 1 . . . 4 setting value, the transducer type level would change to a 1 . . . 5 setting value, and the user level and system level 234 would change to a 1 . . . 6 setting value 237. The modified setting values 236, 237, 238 of the selected operating parameter 220 are stored in storage 130 for retrieval and execution by the imaging modality 110 and/or processor 120.

Figure 5:
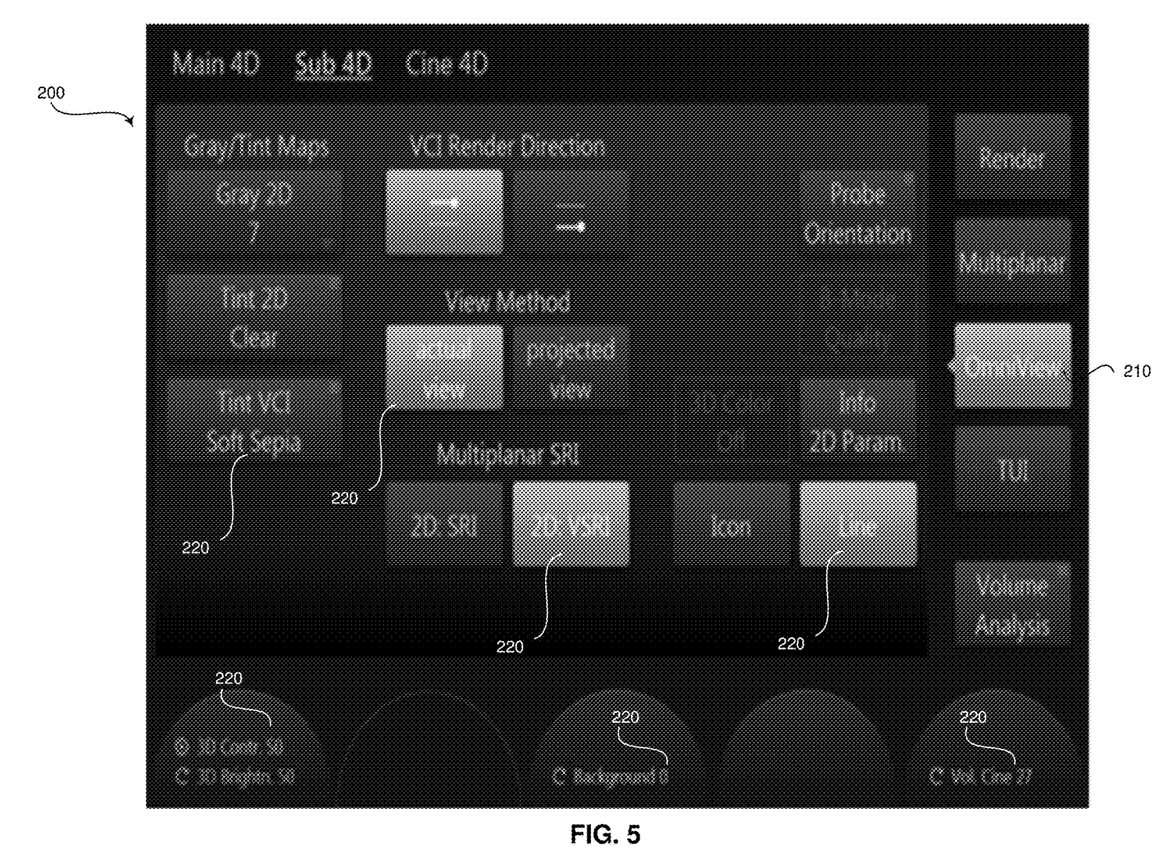
FIG. 5 illustrates an exemplary medical device user interface, in accordance with an embodiment of the invention.
Figure 6:
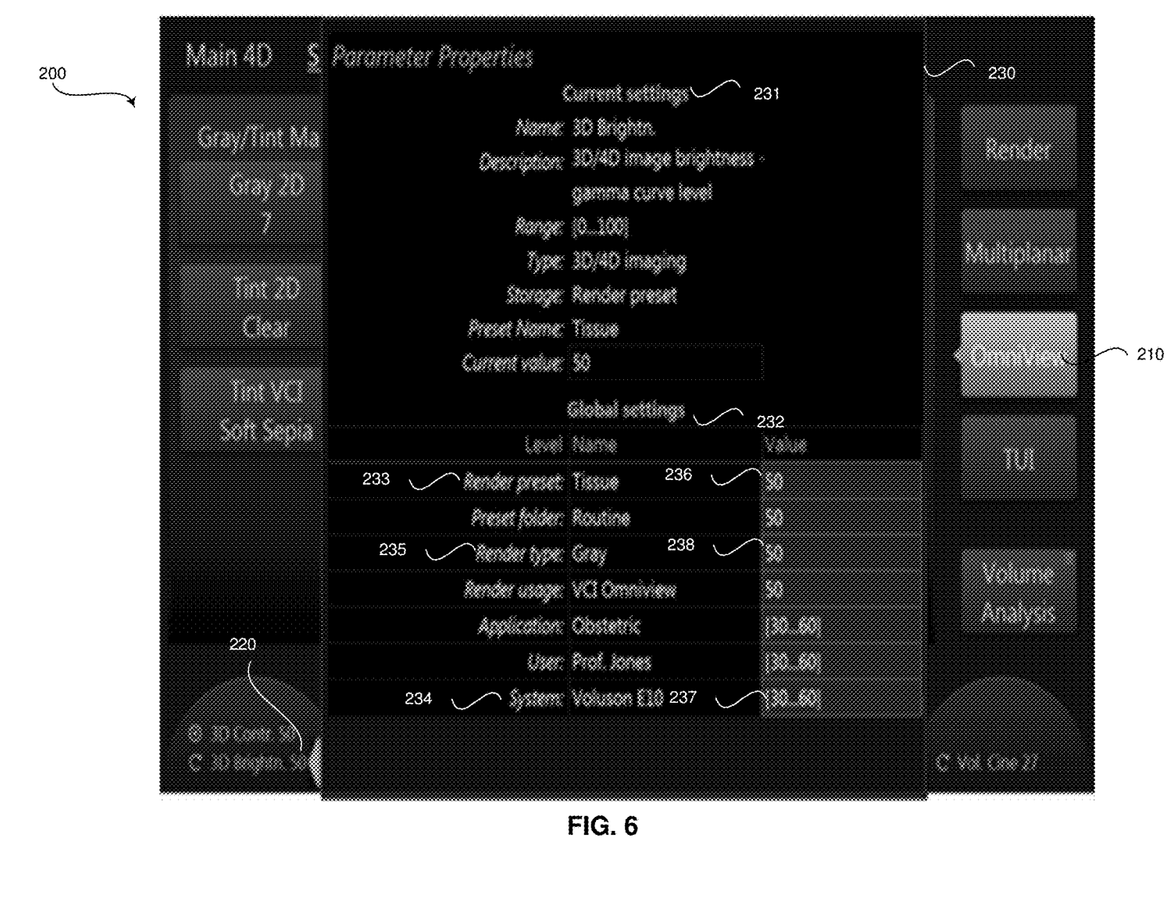
FIG. 6 illustrates an exemplary parameter presentation corresponding with a three-dimensional image brightness operating parameter selected from a medical device user interface of FIG. 5, in accordance with an embodiment of the invention.
Figure 7:
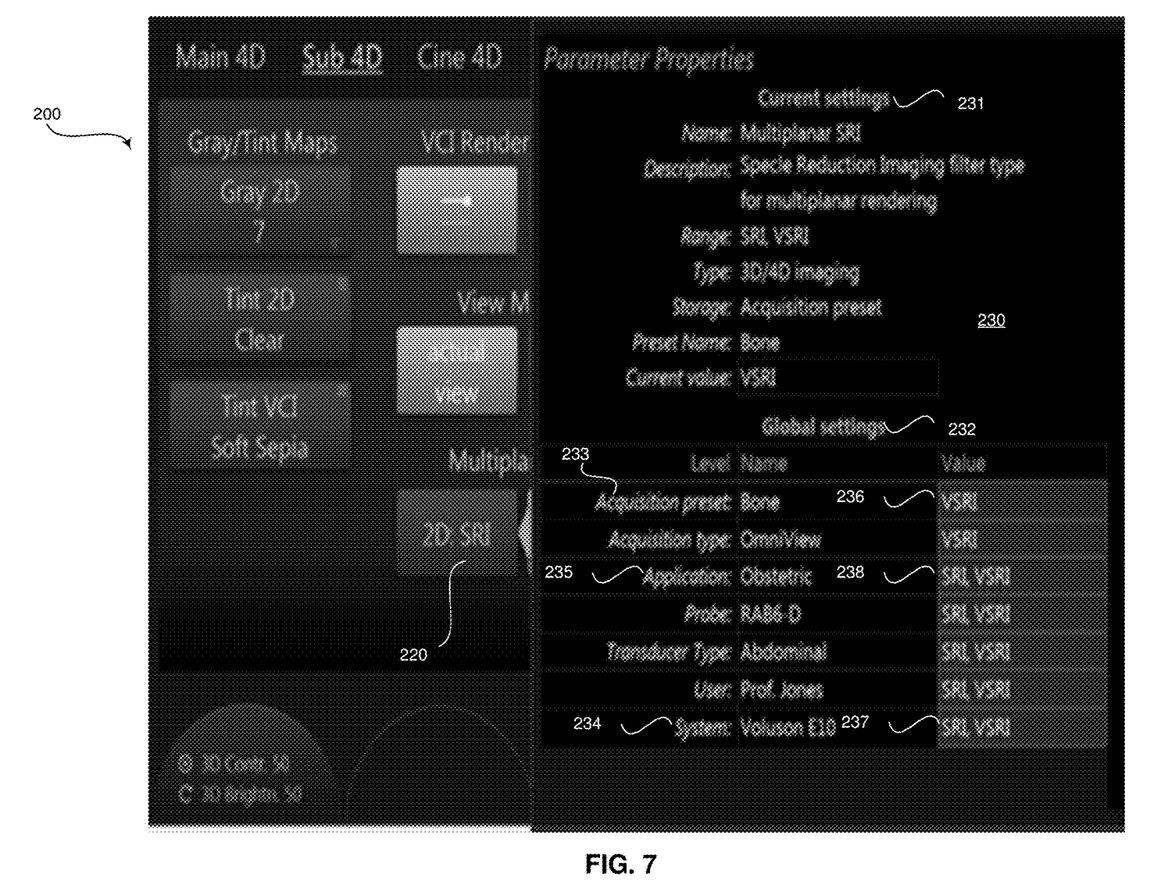
FIG. 7 illustrates an exemplary parameter presentation corresponding with a speckle reduction imaging filter type for multiplanar rendering operating parameter selected from a medical device user interface of FIG. 5, in accordance with an embodiment of the invention.
Figure 8:
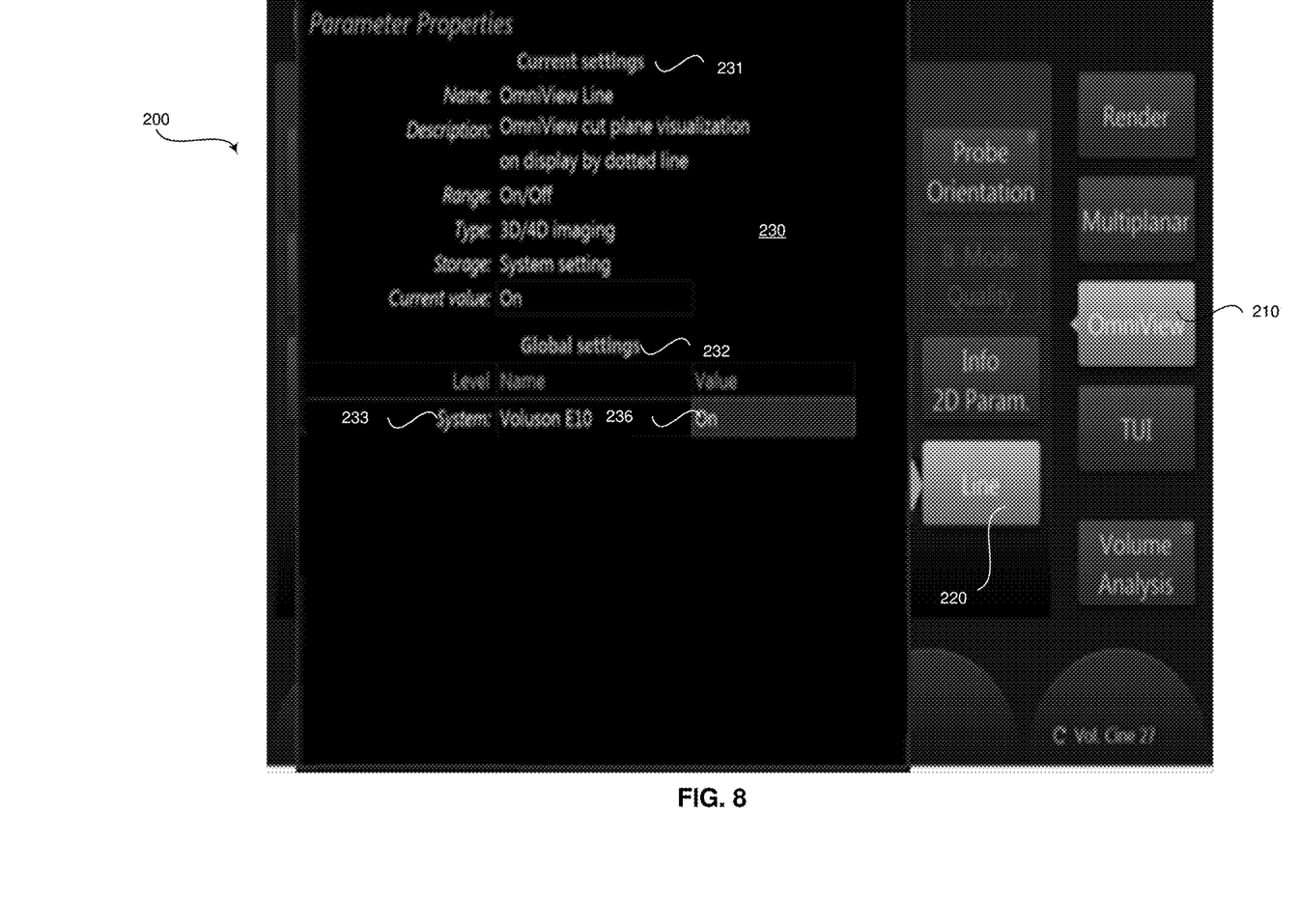
FIG. 8 illustrates an exemplary parameter presentation corresponding with a dotted line display operating parameter selected from a medical device user interface of FIG. 5, in accordance with an embodiment of the invention.

FIG. 5 illustrates an exemplary medical device user interface 200, in accordance with an embodiment of the invention. FIG. 6 illustrates an exemplary parameter presentation 230 corresponding with a three-dimensional image brightness operating parameter 220 selected from a medical device user interface 200 of FIG. 5. FIG. 7 illustrates an exemplary parameter presentation 230 corresponding with a speckle reduction imaging filter type for multiplanar rendering operating parameter 220 selected from a medical device user interface 200 of FIG. 5. FIG. 8 illustrates an exemplary parameter presentation 230 corresponding with a dotted line display operating parameter 220 selected from a medical device user interface 200 of FIG. 5.

Referring to FIGS. 5-8, a medical device user interface 200 comprises selectable examination types 210 and operating parameters 220 corresponding with the selected examination type 210. For example, a user of imaging modality 110 or any suitable medical device may navigate through a medical device user interface 200 to select an examination type 210 and manipulate associated operating parameters 220. With reference to FIG. 5, a user of an ultrasound imaging modality 110 having an abdominal transducer type configured for an obstetric application may select various examination modes 210 such as a rendering mode, a multiplanar mode, an OmniView mode, a tomographic ultrasound imaging (TUI) mode, or a volume analysis, among other things. Each of the examination modes 210 may have corresponding operating parameters 220, such as a 3D/4D image brightness gamma curve level 220 (see FIG. 6), a speckle reduction imaging filter type for multiplanar rendering 220 (see FIG. 7), a dotted line OmniView cut plane visualization 200 (see FIG. 8), and the like.

As illustrated in FIGS. 6-8, selection of an operating parameter 220 prompts a parameter presentation 230 to be presented. The parameter presentation 230 may be a window, such as a pop-up window or any suitable visualization object, for example. The parameter presentation 230 may include information regarding the current settings 231 of the selected operating parameter 220 and the global settings 232 presenting the hierarchical organization of the operating parameter 220. The global settings 232 may include one or more levels 233, 234, 235, each having associated setting values 236, 237, 238. For example, the levels may include a current level 233, a highest level 234, and one or more intermediary levels 235, although more or less levels are also contemplated, as illustrated in FIG. 8, for example. Referring to FIGS. 6-7, the setting values 236, 237, 238 of the levels 233, 234, 235 are consistent such that setting values of lower levels are equal to or within the setting values of the higher levels. In a representative embodiment, the setting values may be numeric values and/or numeric ranges (see FIG. 6), one of a plurality of options (see FIG. 7), an on/off setting (see FIG. 8), or any suitable selectable setting value.

Figure 9:
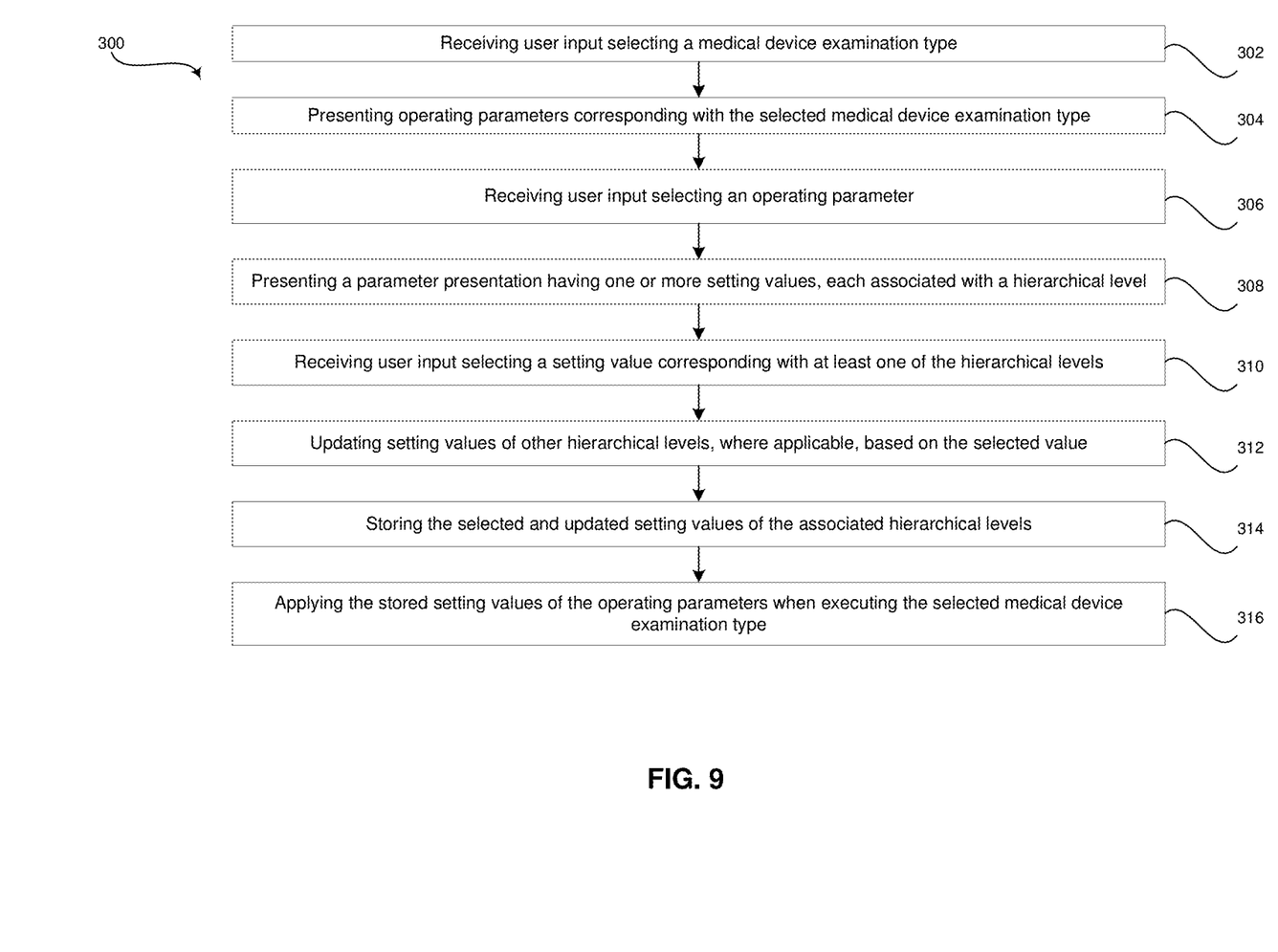
FIG. 9 is a flow chart illustrating exemplary steps that may be utilized for manipulating medical device operating parameters, stored in a hierarchical organization, at different levels of granularity, in accordance with an embodiment of the invention.

FIG. 9 is a flow chart illustrating exemplary steps that may be utilized for manipulating medical device operating parameters, stored in a hierarchical organization, at different levels of granularity, in accordance with an embodiment of the invention. Referring to FIG. 9, there is shown a flow chart 300 comprising exemplary steps 302 through 316. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 302, a user input may be provided that selects an examination type 210 of a medical device 100. For example, a navigable medical device user interface 200 can be displayed at display system 150 by a processor 120. The user input can be provided at a user input module 140 and communicated to the processor 120 for navigating the medical device user interface 200 displayed at a display system 150 to the desired examination type 210. The user input may include button depressions, touchscreen selections, mousing inputs, keyboard inputs, and/or voice commands, among other things, that are received from the user input module 140 and processed by the processor 120 to select the examination type 210.

In step 304, operating parameters 220 corresponding with the selected examination type 210 may be presented at the display system 150. For example, after receiving the examination type 210 selection at step 302, the processor 120 may update the medical device user interface 200 presented at the display system 150 to present the corresponding operating parameters 220 that may be manipulated by a user.

In step 306, a user input can be provided that selects an operating parameter 220. For example, the user input module 140 can receive button depressions, touchscreen selections, mousing inputs, keyboard inputs, and/or voice commands, among other things, that are processed by the processor 120 to select an operating parameter 220 from the medical device user interface 200 presented at the display system 150 to view and/or adjust.

In step 308, a parameter presentation 230 is presented in the medical device user interface 200 at the display system 150. The parameter presentation 230 may be a window, such as a pop-up window or any suitable visualization object. The parameter presentation 230 corresponds with the operating parameter 220 selected at step 306 and may comprise the hierarchical organization of the operating parameter 220. For example, one or more levels 233, 234, 235, each having associated setting values 236, 237, 238 is provided in the parameter presentation 230. The levels can include a current level 233, a highest level 234, and one or more intermediary levels 235. In various embodiments, the parameter presentation 230 may include information regarding the current settings 231 of the selected operating parameter 220.

In step 310, a user input can be provided that selects a setting value 236, 237, 238 associated with one of the hierarchical levels 233, 234, 235 for the operating parameter 220. For example, the user input module 140 can receive button depressions, touchscreen selections, mousing inputs, keyboard inputs, and/or voice commands, among other things, that are processed by the processor 120 to select a setting value 236, 237, 238 within the parameter presentation 230 of the medical device user interface 200 presented at the display system 150. The parameter presentation 230 may comprise a drop-down selection menu 239, a text box, check boxes, radio buttons, or any suitable mechanism for facilitating selection of a setting value 236, 237, 238 for the operating parameter 220.

In step 312, the processor 120 updates the setting values 237, 238 of other hierarchical levels 234, 235, where applicable, based on the setting value 236 selected at step 310. For example, with reference to FIG. 6, if the setting value 236 corresponding with the render preset level 233 is changed from 50 to 60, the setting values 238 associated with the preset folder level, the render type level 235, and the render usage level may be modified to a range from 50 . . . 60 for consistency between the setting values 236, 238 of the levels 233, 235. As another example, with reference to FIG. 7, if the setting value 238 corresponding with the application level 235 is changed from SRI, VSRI to SRI, the setting values 236 associated with the acquisition preset level 233 and the acquisition type level may be changed from VSRI to SRI to maintain consistency between the setting values of the levels. In other words, changes to a setting value 236, 237, 238 of a particular level 233, 234, 235 may cause automatic changes to levels above and/or below the particular level 233, 234, 235 to maintain consistency within the hierarchical organization of the operating parameter 220. Additionally or alternatively, various embodiments provide that the higher levels be manually adjusted to define and/or enable the values available for selection at the lower levels.

In step 314, the modified setting values 236, 237, 238 of the operating parameter 220 are stored at storage 130. In step 316, the stored setting values 236, 237, 238 of the operating parameter 220 are retrieved and applied by the processor 120 when executing the selected medical device examination type 210 at the imaging modality 110 or any suitable medical device.

Aspects of the present invention provide a system 100 and method 300 for manipulating medical device operating parameters 220, stored in a hierarchical organization, at different levels of granularity. In accordance with various embodiments of the invention, a method 300 comprises receiving 306, at a processor 120, first user input selecting an operating parameter 220 of a medical device 110 from a medical device user interface 200 displayed at a display system 150. The method 300 comprises presenting 308, at the display system 150, a parameter presentation 230 prompted by the operating parameter selection 306. In an example embodiment, a plurality of setting values 236, 237, 238 each corresponding to a different hierarchical level 233, 234, 235 of the operating parameter 220 is presented in the parameter presentation 230. The method 300 comprises receiving 310, at the processor 120, second user input manipulating a value of one of the plurality of setting values 236, 237, 238 presented in the parameter presentation 230. The method 300 comprises storing 314, at storage 130, the value of the manipulated one of the plurality of setting values 236, 237, 238.

In a representative embodiment, the method 300 comprises receiving 302, at the processor 120, third user input selecting a medical device examination type 210 from the medical device user interface 200 displayed at the display system 150 and presenting 304, at the display system 150, the operating parameters 220 corresponding with the selected medical device examination type 210 prior to receiving 306 the first user input. In various embodiments, the method 300 comprises automatically updating 312 at least one other value of the plurality of setting values 236, 237, 238 presented in the parameter presentation 230 based on the second user input to maintain consistency between the plurality of setting values 236, 237, 238 at the different hierarchical levels 233, 234, 235 of the operating parameter 220.

In certain embodiments, the at least one other value of the plurality of setting values 236, 237, 238 is at a higher hierarchical level 233, 234, 235 of the operating parameter 220. The at least one other value of the plurality of setting values 236, 237, 238 is broadened to include the value of the manipulated one of the plurality of setting values 236, 237, 238. In a representative embodiment, the at least one other value of the plurality of setting values 236, 237, 238 is at a lower hierarchical level 233, 234, 235 of the operating parameter 220. The at least one other value of the plurality of setting values 236, 237, 238 is narrowed to not exceed the scope of the value of the manipulated one of the plurality of setting values 236, 237, 238.

In various embodiments, options for manipulating the value of the one of the plurality of setting values 236, 237, 238 presented in the parameter presentation 230 is limited based on at least one other value of the plurality of setting values 236, 237, 238 presented in the parameter presentation 230. The at least one other value of the plurality of setting values 236, 237, 238 is at a higher hierarchical level 233, 234, 235 of the operating parameter 220. In certain embodiments, manipulation of the at least one other value of the plurality of setting values 236, 237, 238 changes the options for manipulating the value of the one of the plurality of setting values 236, 237, 238 presented in the parameter presentation 230. In a representative embodiment, the medical device 110 is an imaging modality and the presentation window is a pop-up window. In various embodiments, the method 300 comprises executing the selected medical device examination type 210 and applying 316 the stored value of the manipulated one of the plurality of setting values 236, 237, 238 of the operating parameter 220.

In accordance with various embodiments of the invention, a system 100 comprises a display system 150, a processor 120, and storage 130. The display system 150 is operable to display a medical device user interface 200 and present a parameter presentation 230 comprising a plurality of setting values 236, 237, 238 each corresponding to a different hierarchical level 233, 234, 235 of an operating parameter 220 of a medical device 110. The processor 120 is operable to receive first user input to select the operating parameter 220 from the medical device user interface 200, and receive second user input to manipulate a value of one of the plurality of setting values 236, 237, 238 presented in the parameter presentation 230. The storage 130 is operable to store the value of the manipulated one of the plurality of setting values 236, 237, 238. In various embodiments, the parameter presentation 230 is presented at the display system 150 in response to the first user input selecting the operating parameter 220 from the medical device user interface 200.

In a representative embodiment, the medical device 110 is an imaging modality and the presentation window is a pop-up window. In certain embodiments, the processor 120 is operable to automatically update at least one other value of the plurality of setting values 236, 237, 238 presented in the parameter presentation 230 based on the second user input to maintain consistency between the plurality of setting values 236, 237, 238 at the different hierarchical levels 233, 234, 235 of the operating parameter 220.

In various embodiments, the processor 120 is operable to receive third user input to select a medical device examination type 210 from the medical device user interface 200 displayed at the display system 150. The processor 120 is operable to execute the selected medical device examination type 210. The processor 120 is operable to apply the stored value of the manipulated one of the plurality of setting values 236, 237, 238 of the operating parameter 220. In a representative embodiment, the first, second, and third user input is received at the processor 120 via a touchscreen display user input module 140 of the display system 150. In certain embodiments, the display system 150 is operable to present the operating parameters 220 corresponding with the selected medical device examination type 210.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for manipulating medical device operating parameters, stored in a hierarchical organization, at different levels of granularity.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
   receiving, at a processor, first user input selecting an operating parameter of a medical device from a medical device user interface displayed at a display system, wherein the operating parameter is organized in a hierarchy of a plurality of different hierarchical levels including a higher hierarchical level and a lower hierarchical level that is dependent on the higher hierarchical level, and wherein the operating parameter is executable by the medical device to perform an examination using the medical device;
   presenting, at the display system, a parameter presentation prompted by the operating parameter selection, wherein a plurality of setting values each corresponding to a different one of the plurality of different hierarchical levels of the operating parameter is simultaneously presented in the parameter presentation, and wherein a lower hierarchical level setting value of the plurality of setting values presented in the parameter presentation is equal to or within a higher hierarchical level setting value of the plurality of setting values presented in the parameter presentation;
   receiving, at the processor, second user input manipulating a value of one of the plurality of setting values presented in the parameter presentation;
   storing, at storage, the value of the manipulated one of the plurality of setting values; and
   executing, by the medical device, the stored value of the manipulated one of the plurality of setting values during operation of the medical device.

2. The method according to claim 1, comprising, prior to receiving the first user input:
   receiving, at the processor, third user input selecting a medical device examination type from the medical device user interface displayed at the display system; and
   presenting, at the display system, the operating parameters corresponding with the selected medical device examination type.

3. The method according to claim 2, comprising executing the selected medical device examination type.

4. The method according to claim 1, comprising automatically updating at least one other value of the plurality of setting values presented in the parameter presentation based on the second user input to maintain consistency between the plurality of setting values at the plurality of different hierarchical levels of the operating parameter.

5. The method according to claim 4, wherein the value of the manipulated one of the plurality of setting values is at the lower hierarchical level of the operating parameter, wherein the at least one other value of the plurality of setting values is at the higher hierarchical level of the operating parameter, and wherein the at least one other value of the plurality of setting values is broadened to include the value of the manipulated one of the plurality of setting values.

6. The method according to claim 4, wherein the value of the manipulated one of the plurality of setting values is at the higher hierarchical level of the operating parameter, wherein the at least one other value of the plurality of setting values is at the lower hierarchical level of the operating parameter, and wherein the at least one other value of the plurality of setting values is narrowed to not exceed the scope of the value of the manipulated one of the plurality of setting values.

7. The method according to claim 1, wherein the value of the manipulated one of the plurality of setting values is at the lower hierarchical level of the operating parameter, wherein options for manipulating the value of the one of the plurality of setting values presented in the parameter presentation is limited based on at least one other value of the plurality of setting values presented in the parameter presentation, and wherein the at least one other value of the plurality of setting values is at the higher hierarchical level of the operating parameter.

8. The method according to claim 7, wherein manipulation of the at least one other value of the plurality of setting values changes the options for manipulating the value of the one of the plurality of setting values presented in the parameter presentation.

9. The method according to claim 1, wherein the medical device is an imaging device, and wherein the parameter presentation is a pop-up window.

10. A system, comprising:
a display system operable to:
display a medical device user interface, and
present a parameter presentation comprising a plurality of setting values each corresponding to a different one of a plurality of different hierarchical levels of an operating parameter of a medical device, wherein the operating parameter is organized in a hierarchy of the plurality of different hierarchical levels including a higher hierarchical level and a lower hierarchical level that is dependent on the higher hierarchical level, wherein a lower hierarchical level setting value of the plurality of setting values presented in the parameter presentation is equal to or within a higher hierarchical level setting value of the plurality of setting values presented in the parameter presentation, and wherein the operating parameter is executable by the medical device to perform an examination using the medical device;
a processor operable to:
receive first user input to select the operating parameter from the medical device user interface, and
receive second user input to manipulate a value of one of the plurality of setting values presented in the parameter presentation; and
storage operable to:
store the value of the manipulated one of the plurality of setting values,
wherein the parameter presentation is presented at the display system in response to the first user input selecting the operating parameter from the medical device user interface, and
wherein the stored value of the manipulated one of the plurality of setting values is executed by the medical device during operation of the medical device.

11. The system according to claim 10, wherein the medical device is an imaging device, and wherein the parameter presentation is a pop-up window.

12. The system according to claim 10, wherein the processor is operable to automatically update at least one other value of the plurality of setting values presented in the parameter presentation based on the second user input to maintain consistency between the plurality of setting values at the plurality of different hierarchical levels of the operating parameter.

13. The system according to claim 10, wherein the processor is operable to:
receive third user input to select a medical device examination type from the medical device user interface displayed at the display system, and
execute the selected medical device examination type.

14. The system according to claim 13, wherein the first, second, and third user input is received at the processor via a touchscreen display user input module of the display system.

15. The system according to claim 13, wherein the display system is operable to present the operating parameters corresponding with the selected medical device examination type.

16. A non-transitory computer readable medium having stored thereon, a computer program having at least one code section, the at least one code section being executable by a machine for causing the machine to perform steps comprising:
receiving first user input selecting an operating parameter of a medical device from a medical device user interface displayed at a display system;
presenting a parameter presentation prompted by the operating parameter selection at the display system, wherein a plurality of setting values each corresponding to a different one of a plurality of different hierarchical levels of the operating parameter is simultaneously presented in the parameter presentation, wherein the operating parameter is organized in a hierarchy of the plurality of different hierarchical levels including a higher hierarchical level and a lower hierarchical level that is dependent on the higher hierarchical level, wherein a lower hierarchical level setting value of the plurality of setting values presented in the parameter presentation is equal to or within a higher hierarchical level setting value of the plurality of setting values presented in the parameter presentation, and wherein the operating parameter is executable by the medical device to perform an examination using the medical device;
receiving second user input manipulating a value of one of the plurality of setting values presented in the parameter presentation;
storing the value of the manipulated one of the plurality of setting values; and
executing the stored value of the manipulated one of the plurality of setting values during operation of the medical device.

17. The non-transitory computer readable medium according to claim 16, comprising, prior to receiving the first user input:
receiving third user input selecting a medical device examination type from the medical device user interface displayed at the display system; and
presenting the operating parameters corresponding with the selected medical device examination type at the display system.

18. The non-transitory computer readable medium according to claim 17, comprising executing the selected medical device examination type.

19. The non-transitory computer readable medium according to claim 16, comprising automatically updating at least one other value of the plurality of setting values presented in the parameter presentation based on the second user input to maintain consistency between the plurality of setting values at the plurality of different hierarchical levels of the operating parameter.

20. The non-transitory computer readable medium according to claim 16, wherein the medical device is an imaging device, and wherein the parameter presentation is a pop-up window.

* * * * *